Figure 3:
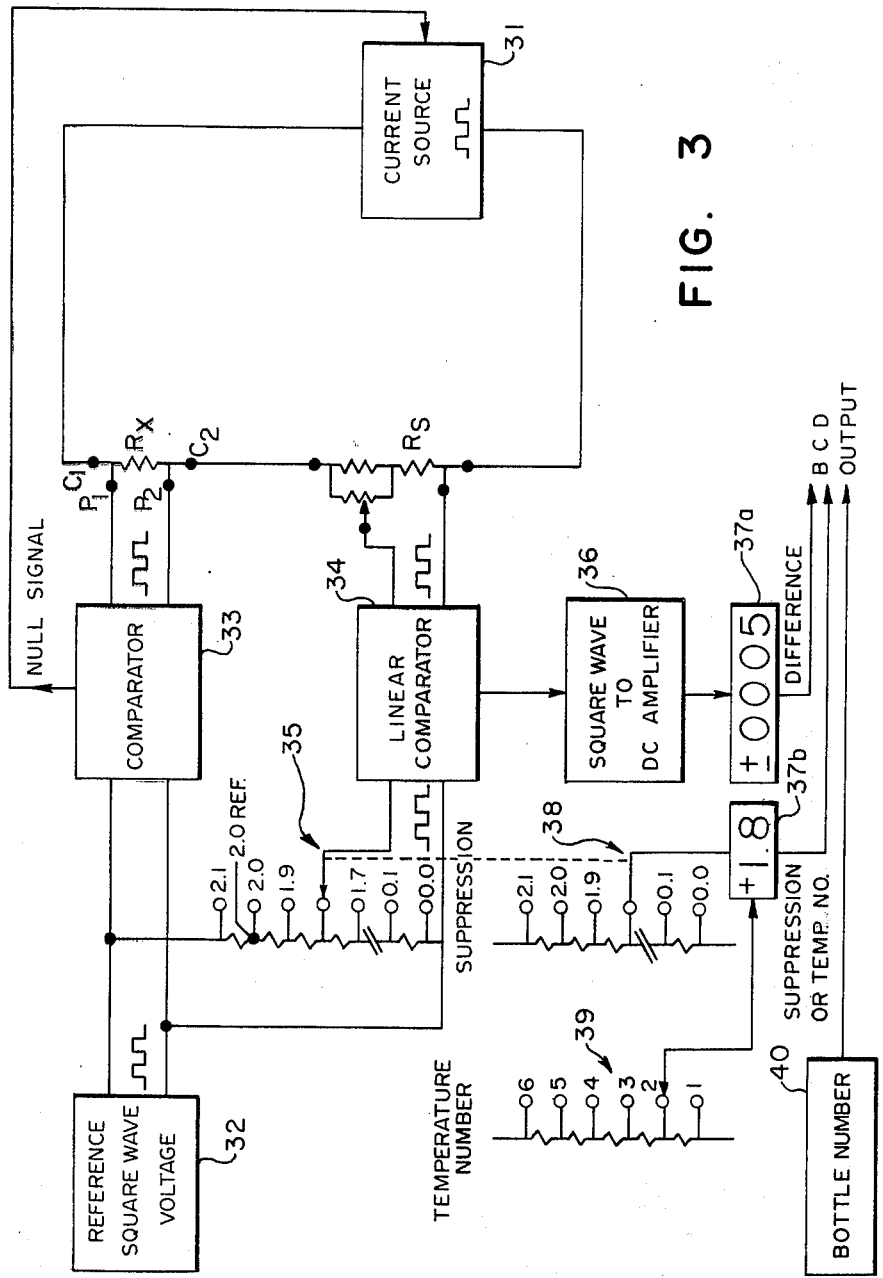

United States Patent [19]
Dauphinee

[11] 3,963,979
[45] June 15, 1976

[54] LIQUID CONDUCTIVITY MEASURING APPARATUS

[75] Inventor: Thomas M. Dauphinee, Ottawa, Canada

[73] Assignee: Canadian Patents and Development Limited, Ottawa, Canada

[22] Filed: Aug. 5, 1974

[21] Appl. No.: 495,100

[52] U.S. Cl. .............................. 324/30; 324/71 E; 204/274
[51] Int. Cl.² ........................................ G01N 27/42
[58] Field of Search ........... 324/30 B, 71 E; 73/421; 23/292; 235/92; 323/22; 204/274

[56] References Cited
UNITED STATES PATENTS

| | | | |
|---|---|---|---|
| 2,901,327 | 8/1959 | Thayer et al. | 324/30 B |
| 3,561,917 | 2/1971 | Michaels et al. | 324/30 B |
| 3,645,802 | 2/1972 | Keough | 324/30 B |
| 3,701,006 | 10/1972 | Volkel | 324/30 B |
| 3,781,675 | 12/1973 | Augel | 324/30 B |

Primary Examiner—R. V. Rolinec
Assistant Examiner—Michael J. Tokar
Attorney, Agent, or Firm—James R. Hughes

[57] ABSTRACT

A salinometer apparatus for measuring the salinity (conductivity) of a liquid sample from a standard sample bottle or other container having an elongated tube having one end adapted for insertion into a sample bottle or container, a conductivity measuring cell formed of a glass tube having an elongated main body portion, four upwardly extending branch tubes connected to the main tube and having liquid seals at their upper ends, metal electrodes mounted inside the four branch tubes, two of the electrodes forming potential electrodes and the other two forming current electrodes, electrical leads passing through the seals and connected to the four electrodes, said cell being connected at one end to the elongated tube and the other to waste, a temperature controlled liquid bath, temperature changing means associated with said bath, an electric heating and control circuit connected to said heating means, the said conductivity cell and a portion of the elongated tube being immersed in said bath, means for flushing the conductivity cell between sample measurements, air pressure means for connection to the sample holder for positively forcing a portion of the liquid sample out of the sample holder into and through the elongated tube and conductivity cell, and a conductivity, measuring circuit connected to the potential and current electrode leads for measuring the conductivity of the liquid contained in the cell.

6 Claims, 5 Drawing Figures

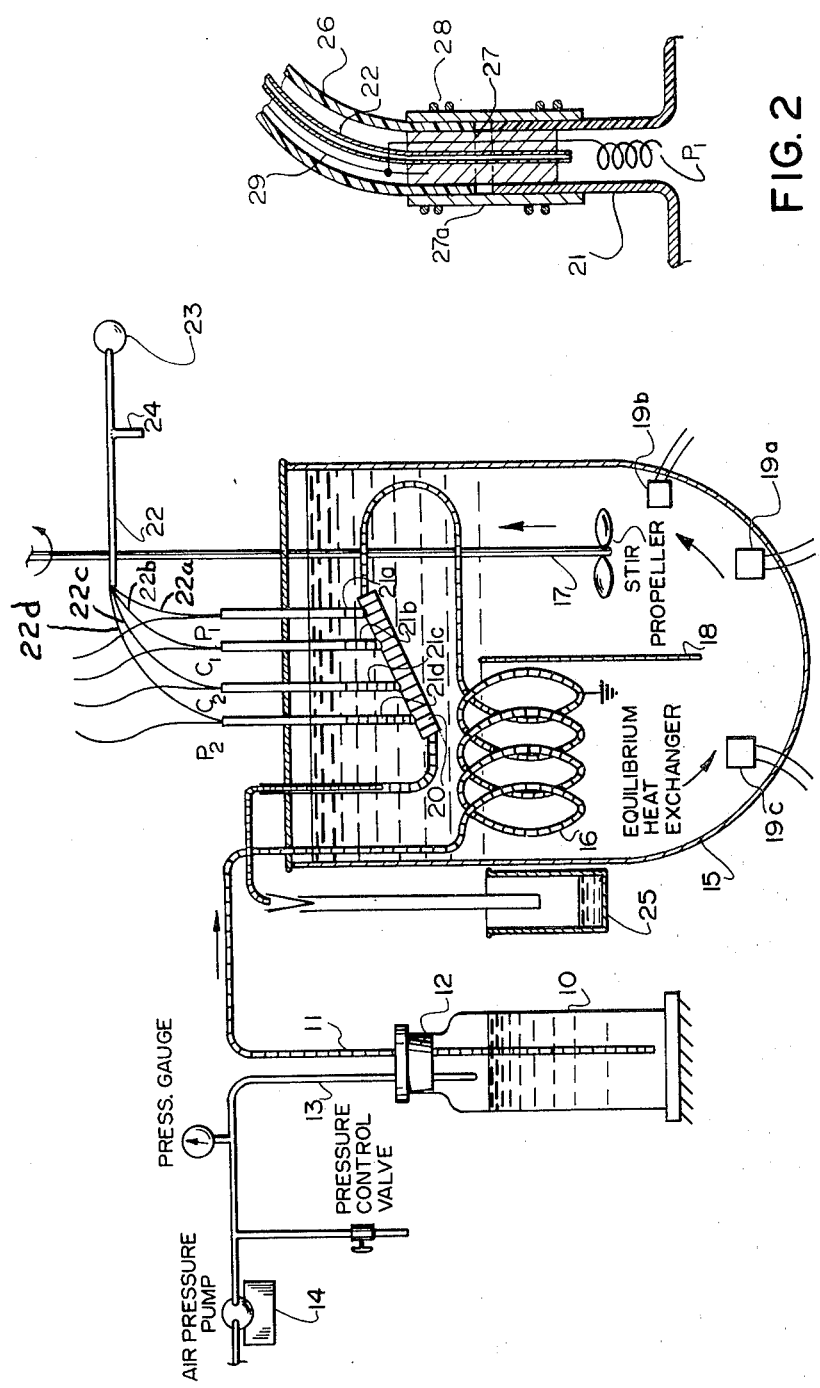

3,963,979

LIQUID CONDUCTIVITY MEASURING APPARATUS

This invention relates to a liquid conductivity measuring apparatus and more particularly to a laboratory salinometer for measurement of sea water samples in conventional sample bottles.

The salinity of seawater is related to conductivity and it is well known that salinity can be measured in this way. There are various techniques and apparatus for measuring conductivity of seawater by sensing apparatus lowered into the sea on the end of a cable. There is also apparatus available for use in laboratories for measuring the conductivity of water samples taken in sample bottles by oceanographic survey organizations and other groups interested in the salinity distribution of sea water in the various bodies of water throughout the world. The latter type of device suffer from certain drawbacks chief of which is slowness in processing, large amounts of sample liquid to make the measurement, and generally low precision of readings unless great care and many corrections are used. In the devices known to applicant, a conductivity cell is used into which the sample liquid is pulled from the sample bottle by suction. In some devices is poured into the measuring system. All devices require isothermal water and some known commercial units use magnetic drive stirring of a fixed quantity after suction filling. Most systems have to accept the cell temperatures, a balance to a null which changes if temperature changes then compensate for temperature or measure the conductivity and then correct. Most of these instruments have a measuring cell of large dimensions; a large amount of sample is required; bubbles form easily causing incorrect readings.

It is an object of the present invention to provide a laboratory type salinometer for measuring the conductivity (salinity) of water samples from standard sample bottles or other sources that gives quick, accurate readings not requiring a large amount of sample.

This and other objects of the invention are achieved by a salinométer apparatus for measuring the salinity (conductivity) of a liquid sample from a standard sample bottle or other container comprising an elongated tube having one end adapted for insertion into a sample bottle or container, a conductivity measuring cell formed of a glass tube having an elongated main body portion, four upwardly extending branch tubes connected to the main tube and having liquid seals at their upper ends, metal electrodes mounted inside the four branch tubes, two of the electrodes forming potential electrodes and the other two forming current electrodes, electrical leads passing through the seals and connected to the four electrodes, said cell being connected at one end to the elongated tube and at the other to waste, a temperature controlled liquid bath, temperature changing means associated with said bath, an electric heating and control circuit connected to said heating means, the said conductivity cell and a portion of the elongated tube being immersed in said bath, means for flushing the conductivity cell between sample measurements, air pressure means for connection to the sample holder for positively forcing a portion of the liquid sample out of the sample holder into and through the elongated tube and conductivity cell, and a conductivity, measuring circuit connected to the potential and current electrode leads for measuring the conductivity of the liquid contained in the cell.

The conductivity measuring circuit may take the form of the circuits shown in U.S. Pat. No. 3,474,330 issued Oct. 21, 1969 to applicant; U.S. Pat. No. 3,495,164 issued Oct. 10, 1970 to applicant; or U.S. Pat. No. 3,757,205 issued Sept. 4, 1973 to applicant. However an improved circuit to that shown in U.S. Pat. No. 3,757,205 is described.

Figure 4:
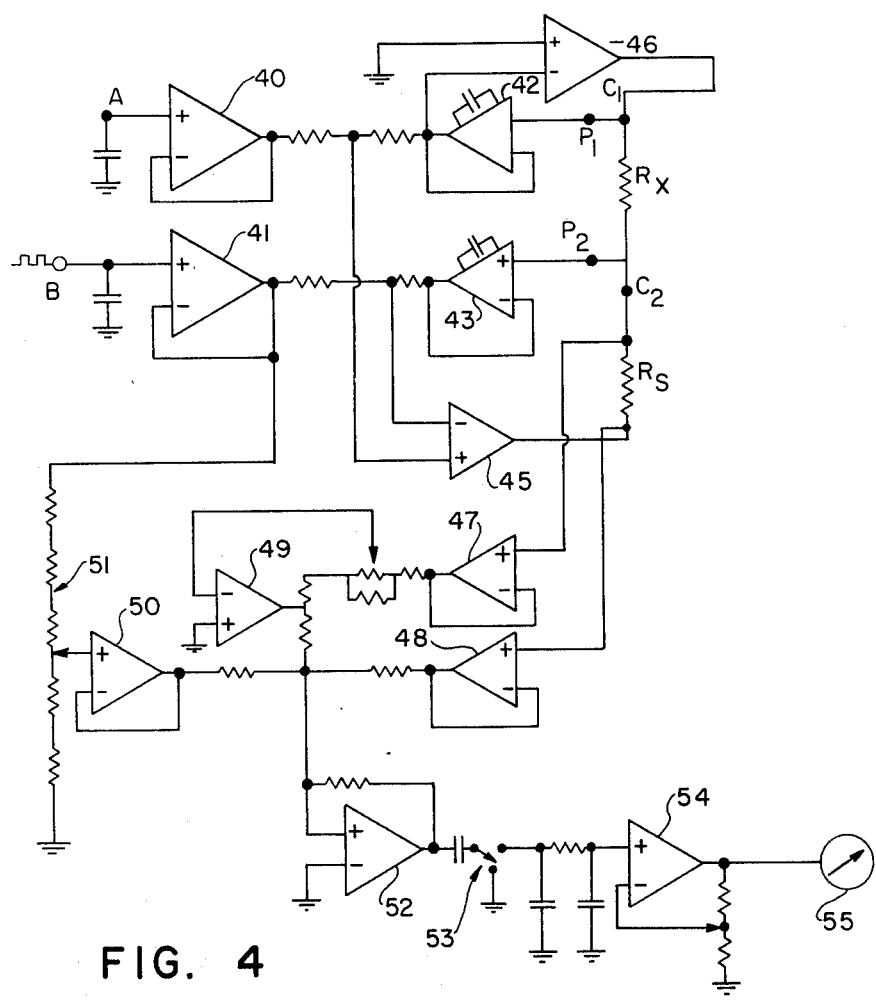
Figure 5:
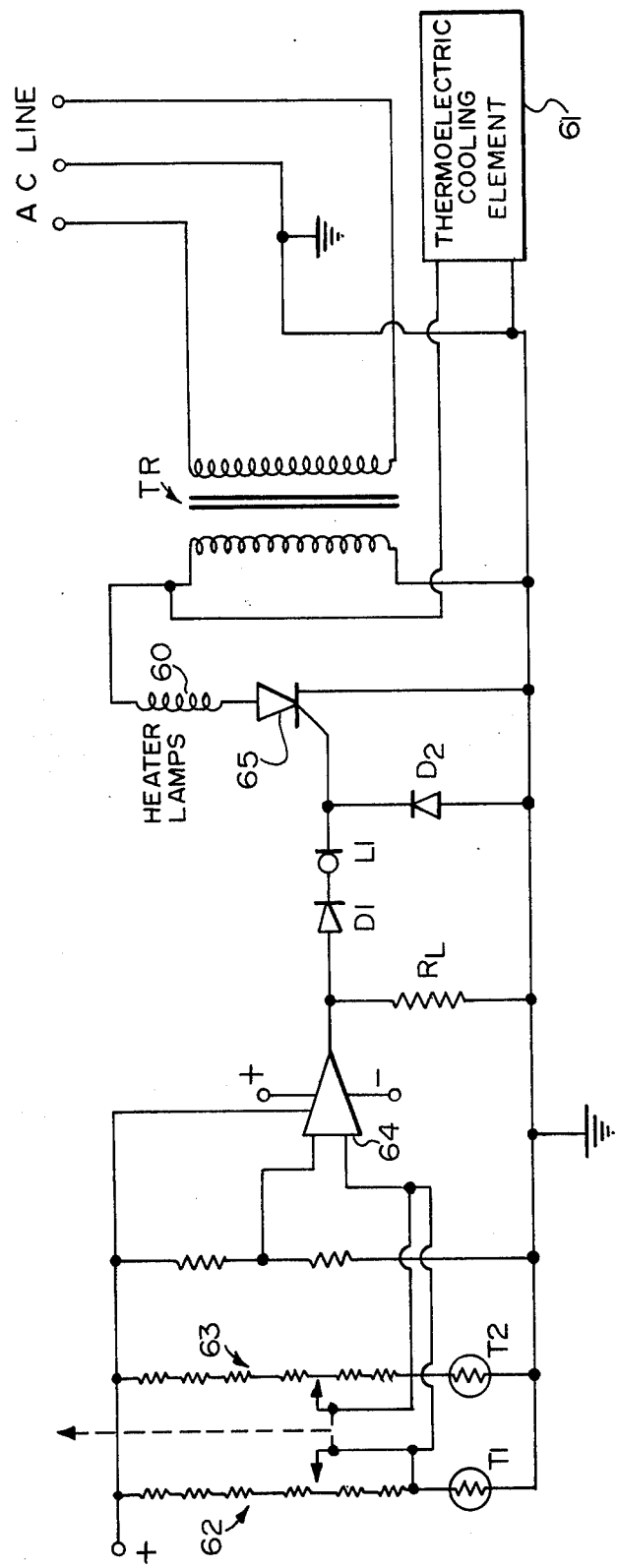

In drawings which illustrate an embodiment of the invention,

FIG. 1 is a cross-section in partly schematic form of the conductivity measuring cell, the temperature controlled water bath, and the pumping means, FIG. 2 is a more detailed cross-section of the conductivity cell and electrodes, FIG. 3 is a block diagram partly schematic of the measuring circuitry, FIG. 4 is a more complete circuit diagram of the measuring circuitry, and FIG. 5 is a power and control circuit for controlling the temperature of the bath.

Referring to FIG. 1, a standard sample bottle 10 containing a liquid sample whose salinity is to be measured has an elongated tube 11 inserted into it through a suitable stopper and sealing means 12. A second tube 13 connected to an air pump 14 which provides a controllable air pressure to the sample bottle is also inserted into the bottle but only extends into the air space above the liquid sample. Tube 11 passes into a temperature controlled water bath 15 preferably forming a series of coils 16. A suitable stirrer 17 and baffle 18 ensure a well mixed and uniform temperature of the liquid through the bath. Electric heating 19a, thermoelectric cooling 19b, and control means 19c are applied to the bath. The electric circuits for these are described in more detail below. Because of the length and small diameter of tube 11, the liquid sample passing through it is rapidly brought to the same temperature as the bath. This tube is connected to a conductivity measuring cell 20 which is also immersed in the bath. The cell comprises a sloping tube portion with the input end higher and the exit end lower and four upwardly extending side tubes 21a, 21b, 21c and 21d. The sloping angle (e.g. 25° to the horizontal) is preferred giving complete and full flushing of the cell. The side tubes have mounted in them electrodes $P_1$, $C_1$, $C_2$ and $P_2$ which constitute the current ($C_1$, $C_2$) and potential ($P_1$, $P_2$) electrodes for the cell. These electrodes, which are of conducting metal preferably platinum-rhodium or other precious metal are formed as a spiral coil and are connected via suitable liquid seals at the upper end to the exterior where they are connected via electrical leads to the measuring circuits. Air inlets 22a, 22b, 22c, and 22d connected to air pump 23 and a control device 24 lead into side tubes 21a, 21b, 21c, and 21d. This arrangement allows efficient and effective flushing of the cell between sample readings and provide an outlet for air allowing the side tubes to fill again after flushing. The sample liquid leaving the cell passes via an insulated tube to an insulated waste bottle. This is necessary with the circuitry to be described so that the cell will not become grounded at any unwanted location. There are other types of circuitry that might be used that would make such isolation unnecessary.

FIG. 2 shows one of the side tubes 21 and the electrode $P_1$ mounted therein in more detail. A rubber tube 26 is connected to tube 21 by means of silicone rubber sealing plug 27 and sleeve 27a with suitable clamping means 28. Air inlet tube 22 passes through the plug into the central portion of the side tube. Electrode $P_1$ is connected via a lead through the plug to make connection with an insulated lead 39 leading to the exterior.

FIG. 3 is a block diagram somewhat schematic in form showing the overall measuring system. The conductivity cell shown here as a resistance $R_x$ has associated with it current electrodes $C_1$ and $C_2$ and potential electrodes $P_1$ and $P_2$. Resistance $R_x$ is connected in series with a reference resistance $R_s$ to a current source 31. A reference square wave voltage source 32 provides a reference voltage to comparator 33 also connected across the potential leads to the cell ($R_x$) and to linear comparator 34 also connected across the reference resistance $R_s$. A suitable calibration step voltage divider network 35 provided for the input to the linear comparator. Any imbalance in the voltages measured in comparator 33 provides a control (null) signal to current source 31 such as to cause this device to provide a current of sufficient magnitude to flow through $R_s$ and $R_x$ to bring comparator 33 to a balance. Imbalance in voltage comparator 34 between the reference square wave voltage from divider 35 and the potential across $R_s$ provides a square wave voltage whose DC magnitude is related to cell conductance (conductivity). This is amplified in square wave to DC amplifier 36 and sent to output reading means 37a which may be a digital voltmeter. The remainder of the apparatus shown provides convenient forms of readout. A voltage divider network 38 ganged to network 35 provides convenience in reading the setting of the voltage divider network 35 with a second output reading means 37b. A temperature number resistance network 39 provides a temperature setting bias for the readout. It should be pointed out that the output reading is a sum of the readings shown on 37b and 37a and the calibration is in terms of the ratio of conductance of the water under test to the conductance of standard water commonly called Copenhagen Standard Seawater. The arrangement shown is somewhat arbitrary and for convenience works with the standard set at 2.0 + · 00000. Various other readout arrangements may be used. A bottle number counter 40 provides a coded signal for automated output readings and a coded switch can also be used to give the setting of the voltage divider network 35 in place of divider 38 and voltage measuring means 37b.

Referring to FIG. 4, a more complete electrical measuring circuit is shown. A regulated square wave voltage is applied at point B and this voltage is compared in a comparator made up of amplifier 40 and 41 and amplifier 42 and 43 which receive an input from the potential across potential electrodes $P_1$ and $P_2$ of the salinity cell whose resistance is indicated as $R_x$. A null is obtained by the comparator circuit, which is in effect a bridge, by amplifier 45 which acts as a current source driving a current of the correct amplitude and sense through the salinity cell (via current electrodes C2 and C1) to achieve a null at the comparator. The current from the current source also passes through standard resistance $R_s$. Amplifier 46 provides a current that tends to balance the current injected into the cell by amplifier 45 and maintains a constant low potential at potential lead $P_1$. The voltage across $R_s$ which is a measure of the conductance of the cell and hence of the conductivity of the seawater sample is compared in a linear comparator made up of amplifiers 47 and 48 and amplifier 49 and 50 where this voltage is compared with a square wave voltage obtained across a resistance network 51 connected to the output of amplifier 41 and thus the regulated square wave voltage applied to B. The network comprises resistance steps suitable to cover necessary measurement ranges. The output of the linear comparator in the form of a square wave is amplified and converted to DC by amplifier 52 and demodulating switch 53 and is further amplified by amplifier 54 to a level suitable for the output meter 55, e.g. a digital voltmeter.

Referring to FIG. 5, a preferred form of temperature control circuit for ther thermostatted bath 15 (of FIG. 1) has heating lamps 60 (19a of FIG. 1) and thermoelectric cooling elements 61 (19b of FIG. 1) which would be placed in thermal relation with the liquid in bath 15. These elements are energized from an AC line via isolating transformer TR. Although the cooling is energized at all times, power to the heater lamps is controlled by two thermistors T1 and T2 (19c of FIG. 1) with suitable range setting resistance networks 62 and 63 which provide an input into amplifier 64 and load resistor $R_L$. The thermistors are placed in the bath preferably in direct line of sight of light from the heater lamps and operate rapidly giving a series of "on-off" switching signals that provide quick effective control. It has been found that this arrangement provides a precise and predictive method of control. The output of the amplifier passes to diodes D1 and D2 that prevent unwanted AC effects and current limited L1 and then to the control electrode of SCR power switch 65.

In operation to obtain the conductivity ratio, a measurement is carried out passing a standard solution (STD). i.e. Copenhagen Standard Seawater, through the cell at the same control temperature as that of the sample ($x$) under test, the conductivity ratio is then given by:

$$\frac{\text{Reading } x}{\text{Reading STD.}}$$

Taken at the same temperature. From this and known data the conductivity can be calculated for any temperature and, to obtain salinity, known equations relating this ratio to salinity at any temperature can be used. It is convenient to adjust reference resistor $R_s$ to cause the conductance reading for the standard water to be an even number i.e. 1.00000 or 2.00000.

I claim:

1. A liquid conductivity measuring apparatus for measuring the salinity of a liquid sample from a standard sample bottle or other container comprising:
    a. an elongated tube having one end adapted for insertion into a sample bottle or container,
    b. a measuring cell for measuring the conductivity of a water sample formed of a tube having an elongated main body portion connected at one end to the elongated tube and at the other to waste, four upwardly extending branch tubes connected to the main tube and having liquid seals at their upper ends, electrodes mounted inside the four branch tubes, two of the electrodes forming potential electrodes and the other two forming current electrodes, electrical leads passing through the seals and connected to the four electrodes,
    c. means for controlling the temperature of said cell, d. means for flushing the contents of the cell to waste between sample measurements, and
e. air pressure means for connection to the sample holder for positively forcing a portion of the liquid sample out of the sample holder into and through the said tube and into the means for measuring the conductivity, and
f. a conductivity measuring circuit connected to the potential and current electrode leads for measuring the conductivity of the liquid sample in the cell said circuit comprising: a standard resistance, a current source connected in series with the standard resistance and the current electrodes of the cell, a voltage comparator connected to the potential electrodes of the cell and to a source of regulated square wave voltage such as to compare the voltage across the potential electrodes and the square wave voltage such as to cause it to provide a current through the standard resistance and the current electrodes such that the voltage comparator is brought to a null, a linear voltage comparator connected across the standard resistance and to a voltage related to the regulated square wave voltage to compare this voltage and the voltage across the standard resistance and provide an output square wave voltage related to the conductivity of the cell, a square wave to DC amplifier connected to the linear voltage comparator for changing the output voltage to DC, a DC amplifier connected to the square wave to DC amplifier, and readout means connected to the DC amplifier.

2. A liquid conductivity measuring apparatus for measuring the salinity of a liquid sample from a standard sample bottle or other container comprising:
   a. an elongated, thin-walled heat exchange tube having one end adapted for insertion into a sample bottle or container, said tube having a relatively small diameter and being made of a material having high heat conductivity characteristics,
   b. a conductivity measuring cell connected to the other end of the elongated tube and to waste,
   c. a liquid bath with the conductivity measuring cell and a portion of the elongated tube immersed in the said bath such that, on passage of a liquid through the tube into the cell, its temperature rapidly approximates that of the liquid bath,
   d. means for measuring the temperature of said liquid bath,
   e. air pressure means for connection to the sample holder for positively forcing a portion of the liquid sample out of the sample holder into and through the said tube and into the conductivity measuring cell, and
   f. means for flushing the contents of the said conductivity measuring cell to waste between sample measurements.

3. A liquid conductivity measuring apparatus as in claim 2 wherein the conductivity measuring cell is formed of a tube having an elongated main body portion connected at one end to the elongated tube and the other to waste, four upwardly extending branch tubes connected to the main tube and having liquid seals at their upper ends, electrodes mounted inside the four branch tubes, two of the electrodes forming potential electrodes and the other two forming current electrodes, electrical leads passing through the seals and connected to the four electrodes, and a conductivity measuring circuit connected to the said leads.

4. A liquid conductivity measuring apparatus as in claim 3 wherein the means for flushing the conductivity cell is a source of air connected to one of the said branch tubes such that on introduction of air, the cell is cleared of liquid.

5. A liquid conductivity measuring apparatus as in claim 2 wherein the means for measuring the temperature of said liquid bath is a temperature control means including a heating lamp connected to an electrical supply, thermoelectric cooling device connected to an electrical supply, and at least one thermistor immersed in the bath in spaced relation to the lamp and connected in the electrical supply to the heating lamp for turning on and off said lamp to effect thermostatic control of the bath.

6. A liquid conductivity measuring apparatus as in claim 3, wherein the conductivity cell is positioned in the apparatus such that the end connected to waste is lower than the end connected to the elongated tube and the means for flushing the conductivity cell is a controllable source of gas pressure connected to each of the four upwardly extending branch tubes.

* * * * *